(12) United States Patent
Gioventù et al.

(10) Patent No.: US 9,161,528 B2
(45) Date of Patent: Oct. 20, 2015

(54) METHOD FOR DENTAL PULP CRYOPRESERVATION

(75) Inventors: Silvia Gioventù, Milan (IT); Stefania Frasca, Ragusa (IT); Elisa Giovanna Angela Montelatici, Milan (IT); Paolo Rebulla, Milan (IT); Gabriella Andriolo, Como (IT); Lorenza Lazzari, Milan (IT); Ferruccio Bonino, Pisa (IT)

(73) Assignee: FONDAZIONE IRCCS "CA' GRANDA—OSPEDALE MAGGIORE POLICLINICO", Milan (IT)

( * ) Notice: Subject to any disclaimer, the term of this patent is extended or adjusted under 35 U.S.C. 154(b) by 0 days.

(21) Appl. No.: 13/697,244

(22) PCT Filed: May 6, 2011

(86) PCT No.: PCT/IB2011/000966
§ 371 (c)(1),
(2), (4) Date: Jan. 16, 2013

(87) PCT Pub. No.: WO2011/141789
PCT Pub. Date: Nov. 17, 2011

(65) Prior Publication Data
US 2013/0217123 A1    Aug. 22, 2013

(30) Foreign Application Priority Data

May 12, 2010 (IT) .............................. MI2010A0839

(51) Int. Cl.
*C12N 5/00* (2006.01)
*A01N 1/02* (2006.01)
*A61K 35/32* (2015.01)
*C12N 5/0775* (2010.01)
*C12N 5/077* (2010.01)

(52) U.S. Cl.
CPC ................ *A01N 1/0284* (2013.01); *A01N 1/02* (2013.01); *A61K 35/32* (2013.01); *C12N 5/0653* (2013.01); *C12N 5/0654* (2013.01); *C12N 5/0655* (2013.01); *C12N 5/0664* (2013.01)

(58) Field of Classification Search
USPC .................................................. 435/374, 325
See application file for complete search history.

(56) References Cited

U.S. PATENT DOCUMENTS

| 5,846,080 | A  | * | 12/1998 | Schneider ...................... 433/215 |
| 2003/0068305 | A1 | | 4/2003 | Sramek et al. |
| 2005/0014256 | A1 | | 1/2005 | Sramek |
| 2006/0252151 | A1 | | 11/2006 | Sramek |
| 2007/0190518 | A1 | * | 8/2007 | Bourgeois et al. ............. 435/1.1 |

FOREIGN PATENT DOCUMENTS

WO        2007070883 A2     6/2007

OTHER PUBLICATIONS

Woods et al., Optimized cryopreservation method for human dental-pulp derived stem cells and their tissues of origin for banking and clinical use. Cryobiology, vol. 59 (Jun. 16, 2009) pp. 150-157.*
Miura et al., SHED: Stem cells from human exfoliated deciduous teeth. Proceedings of the National Academy of Sciences, vol. 100, No. 10 (May 13, 2003) pp. 5807-5812.*

* cited by examiner

*Primary Examiner* — Laura Schuberg
*Assistant Examiner* — Kara Johnson
(74) *Attorney, Agent, or Firm* — Pearne & Gordon LLP

(57) ABSTRACT

The present invention relates to a method for cryopreserving the pulp of a non-exfoliated deciduous tooth, comprising a step of making with a laser a hole into the tooth removed from its physiological seat on the tooth neck. After making the hole, the tooth is contacted with a cryopreserving agent and then cryofrozen. An object of the invention further consists in mesenchymal stem cells isolated from the pulp of a cryopreserved tooth according to the method of the invention.

17 Claims, 8 Drawing Sheets

METHOD FOR DENTAL PULP CRYOPRESERVATION

The present invention relates to a method for cryopreserving the pulp of a tooth in order to isolate stem cells, in particular mesenchymal stem cells, from the pulp. Adult stem cells are an inexhaustible source of multipotent cells, which can differentiate—if required—into various cell lines. Thanks to this property, adult stem cells can be used in the field of regenerative medicine to various purposes. For instance, the manifold therapeutic properties of stem cells taken from blood or bone marrow allowed—though to a limited extent—to solve diseases that once were believed to be incurable.

These properties of adult stem cells have recently raised a growing interest in scientists, who have made great efforts in order to obtain stem cells from various tissue sources.

A particularly interesting source of stem cells is dental pulp. It was indeed proven that this tissue is an excellent reservoir of stem cells with one of the highest ratios stem cells/tissue mass ever found.

Stem cells derived form dental pulp have a considerable proliferative level and cell plasticity and this is a very important aspect for possible therapeutic applications. The stem cells of the dental pulp can give rise to different cells of mesenchymal origin, such as e.g. osteoblasts, adipocytes, chondrocytes, striated muscle cells, as well as to cells of non-mesenchymal origin, such as e.g. melanocytes.

In particular, by transplanting stem cells of dental pulp onto animal gingiva it was proven that these cells can generate ex novo nerves, bones, cartilage and teeth. Currently, the applications that make use of stems cells deriving from dental pulp are focused on bone regeneration both in the dental and maxillo-facial field (briefly, in the future it might be possible to regenerate teeth and the periodontium supporting them directly in the anatomical site) and in the orthopedic field.

In the meanwhile specific studies are being made in order to verify the future possible use of stem cells from dental pulp to autologous or allogenic purposes. Results are encouraging and indicate that these stem cells can also be used for muscle and nerve regeneration and for supporting the stability of fat tissue.

Another advantage of the dental pulp is that it is a very rich and potentially inexhaustible source of stem cells, thanks to the large number of teeth that might potentially be used for extracting this tissue.

In the light of the potentialities of the stem cells deriving from the pulp as described above, scientists have raised the problem of how these cells can be preserved and "banked" for possible future therapeutic uses, either autologous or allogenic.

Methods for preserving and banking stem cells deriving from the dental pulp are known in the field. For instance, in some specialized biobanks, in order to cryopreserve the stems cells of the dental pulp, a protocol is used including a step in which the tooth is broken so as to extract the dental pulp, followed by a step in which the pulp is treated so as to recover the stem cells contained therein. Stem cells are then stored in liquid nitrogen after being amplified.

As an alternative to the method of cryopreservation of stem cells extracted from a tooth, it is known about methods in which an intact tooth, extracted from its seat, is subjected to cryopreservation and banking. The aim of cryopreserving and banking an intact tooth is to recover the pulp and the stem cells contained therein in a following step, only when there is an actual therapeutic need.

The first of the approaches described above enables to recover stem cells from the dental pulp, e.g. mesenchymal stem cells, with a high effectiveness in terms of yield and cell vitality. However, this method has the disadvantage of being quite expensive both in terms of time needed for recovering and amplifying the cells and from an economic point of view.

As a matter of fact, a person interested in this method of cryopreservation is forced to bear quite high costs when taking the tooth out, without being sure yet of a possible future therapeutic use. Indeed, this method includes taking the tooth out, crushing it for recovering the pulp and eventually isolating and growing the stem cells contained therein for cryopreserving them later; this without being sure that during his/her life the same person will face the actual need to use the cryopreserved cells to a therapeutic purpose.

Conversely, the method of cryopreserving the intact tooth has the advantage of being faster and less expensive for the body in charge of cryopreservation and, as a consequence, for the person interested in cryopreserving the tooth.

However, the cryopreservation of an intact tooth does not necessarily ensure an absolute success when thawing said tooth, both as far as the recovery percentages of stem cells are concerned and in terms of quality of recovered cells.

The extent and the result of possible applications will depend on the amount and quality of recovered stem cells. The stems cells recovered in a step following cryopreservation must still have the proliferative and differentiative capacity characterizing stem cells isolated from the pulp of a fresh tooth, not subjected to cryopreservation.

Recovery percentages of stem cells and the quality of the recovered cells after thawing a cryopreserved whole tooth are not fully satisfactory. This is probably due to the fact that tooth enamel is a little porous, very hard material, resistant to various chemicals, just because of its biological function. These properties are however disadvantageous as far as the success of cryopreservation in terms of recovery percentages of the cells and of vitality after thawing is concerned.

The technical problem underlying the present invention is to provide a method for the cryopreservation of dental pulp (and therefore of the stem cells contained therein) that is simple and cheap and at the same time ensures good results in terms of post-thawing recovery percentages and of vitality of the cells, taking into particular consideration their proliferative and differentiative capacity.

This problem is solved by a method for cryopreserving the dental pulp as outlined in the appended claims.

The present invention relates to a method for cryopreserving the pulp of a tooth, comprising the following steps:
(a) making at least one hole into said tooth so as to reach at least the dentine;
(b) put the tooth thus pierced in contact with a cryopreserving agent;
(c) adjusting the tooth in contact with the cryopreserving agent to a cryofreezing temperature.

The method according to the invention can also be defined as a method for cryopreserving a tooth containing dental pulp, and a method for cryopreserving pulp stem cells, in particular mesenchymal stem cells.

As a an alternative, the method according to the invention can be defined as a method for banking dental pulp, and a method for banking stem cells, in particular mesenchymal stem cells, from dental pulp. Another possible definition of the method according to the invention is a method for banking teeth comprising at least one hole reaching at least the dentine.

The at least one hole is a microhole preferably made with a laser having such a wavelength as to be able to pierce a hard tissue such as the enamel and a hard, porous tissue such as the dentine.

The use of such a laser enables to remove in an extremely accurate and selective manner portions of dental enamel and of dentine and, in an embodiment, to access the root canals without running the risk of removing, tearing or overheating the dental pulp. These properties contribute to ensure an optimal cryopreservation of the tooth and of the pulp material, since the risk of bacterial contamination during the procedure is very low because the exposition area of the pulp material is highly limited.

Moreover, the laser used in the method according to the invention ensures the absolute integrity of the cryopreserved dental tissue without any risk of microfractures of the tooth.

The aim of tooth piercing is to increase the porosity thereof, thus enabling the cryopreserving agent to penetrate the tooth at least as far as the dentine layer and to get diffused therein. This allows to improve cryopreservation performances in terms of recovery percentages of the stem cells and of cell vitality (proliferative and differentiative capacity) after thawing.

As a matter of fact, the improvement of tooth cryopreservation performances enables to recover at a later step a population of stem cells of the dental pulp with quantitative and qualitative properties that can be compared with those of stem cells isolated from the pulp of a fresh tooth, not subjected to cryopreservation. Moreover the quantitative and qualitative properties of the recovered stem cells are higher than those of stem cells obtained after thawing a non-pierced whole tooth, as shown in the experimental section of the present patent application.

The stem cells contained in the dental pulp can be recovered with any method known in the field. In the framework of the present invention, the cryopreserved tooth is mechanically broken after thawing and the dental pulp is extracted. Then the dental pulp is subjected to treatments known in the field for recovering and amplifying the stem cells contained therein, in particular mesenchymal stem cells, which will be later used for various applications for tissue regeneration or replacement.

The present invention is described below in a detailed manner, also with reference to the accompanying figures, in which.

Figure 3:
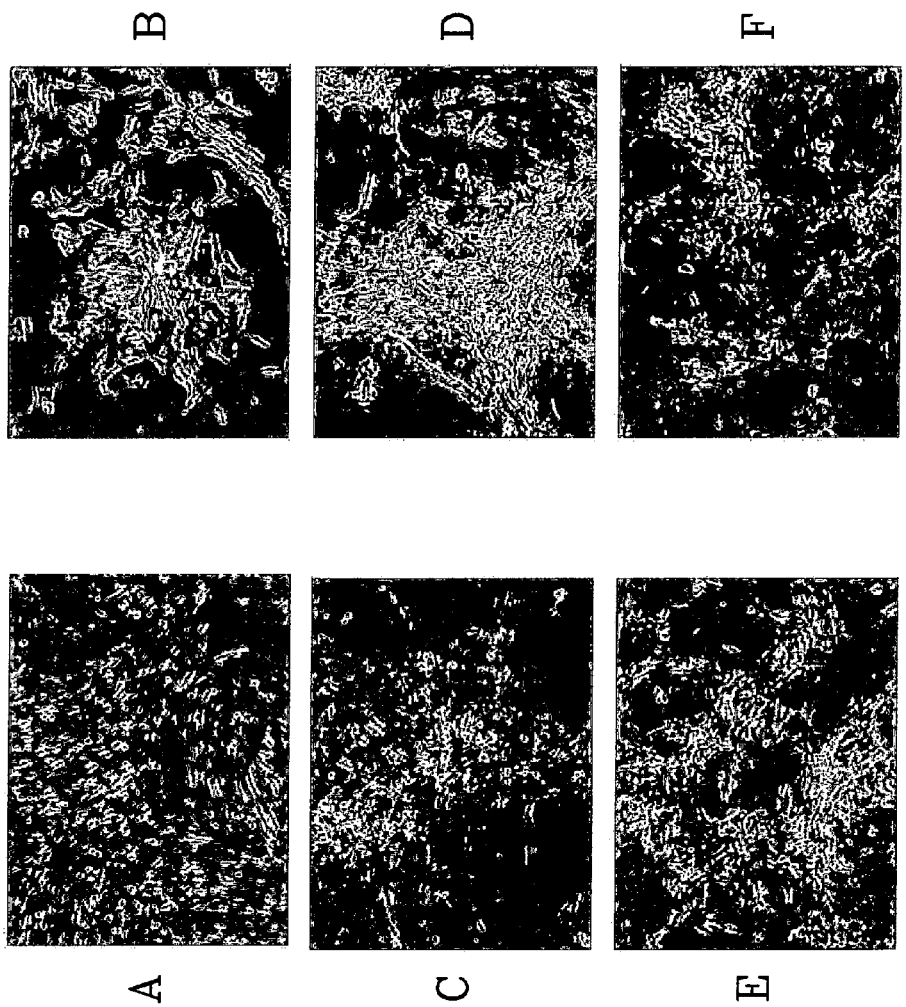
Figure 4:
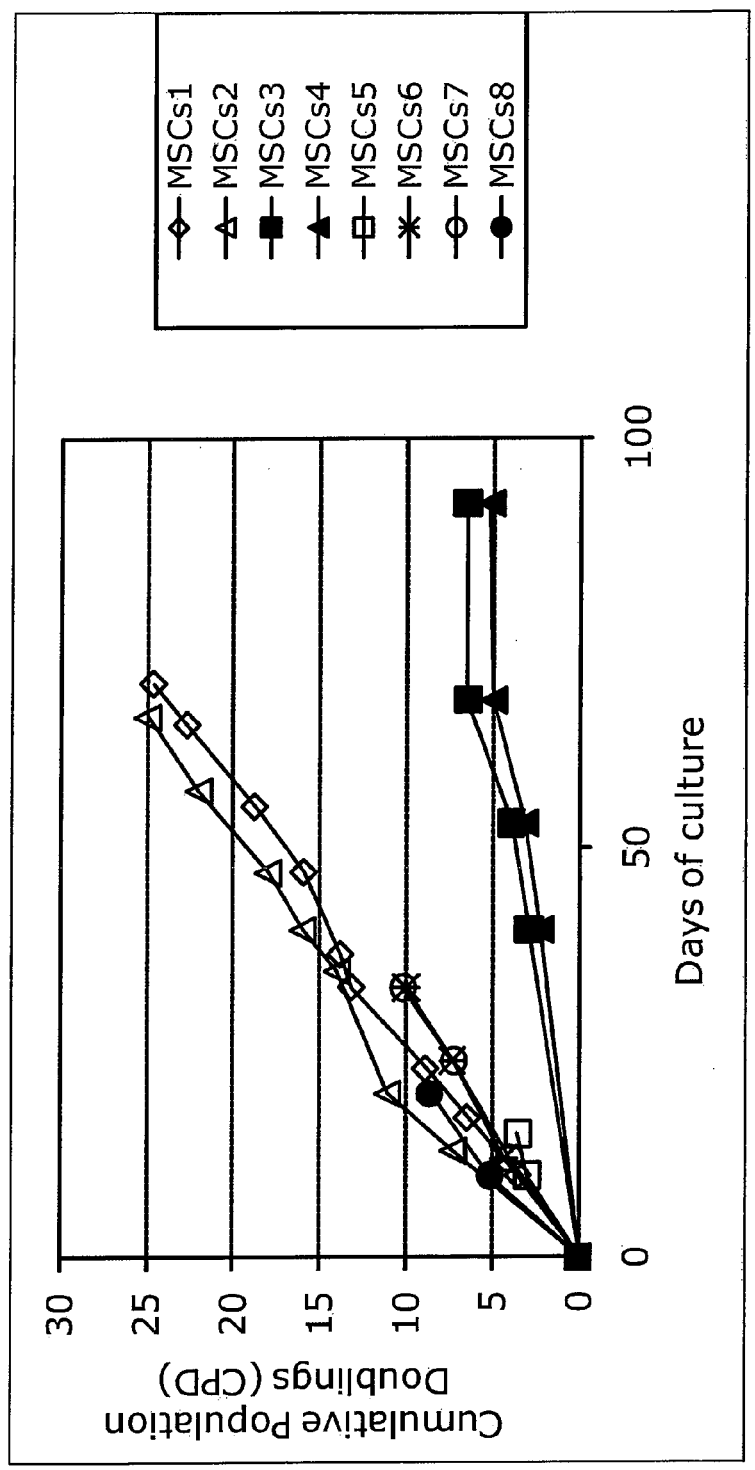
Figure 5A:
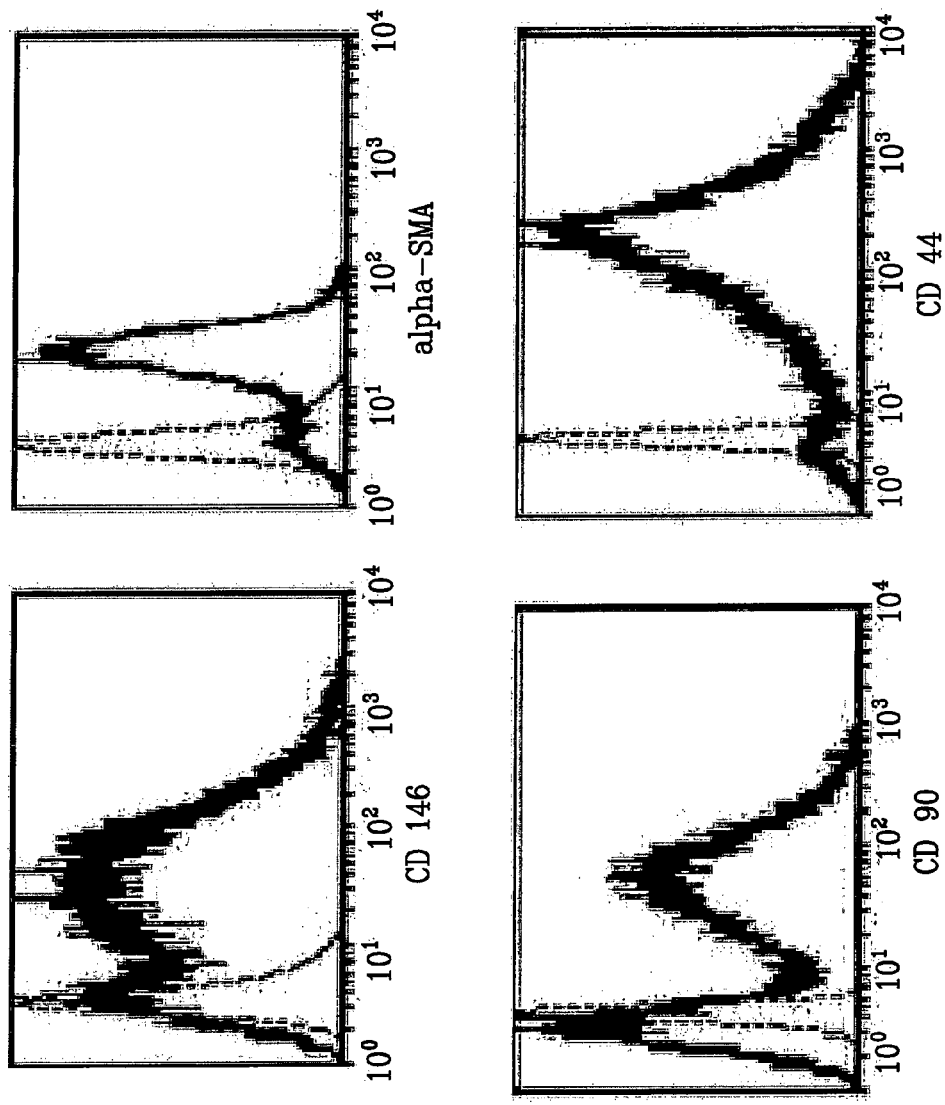
Figure 5B:
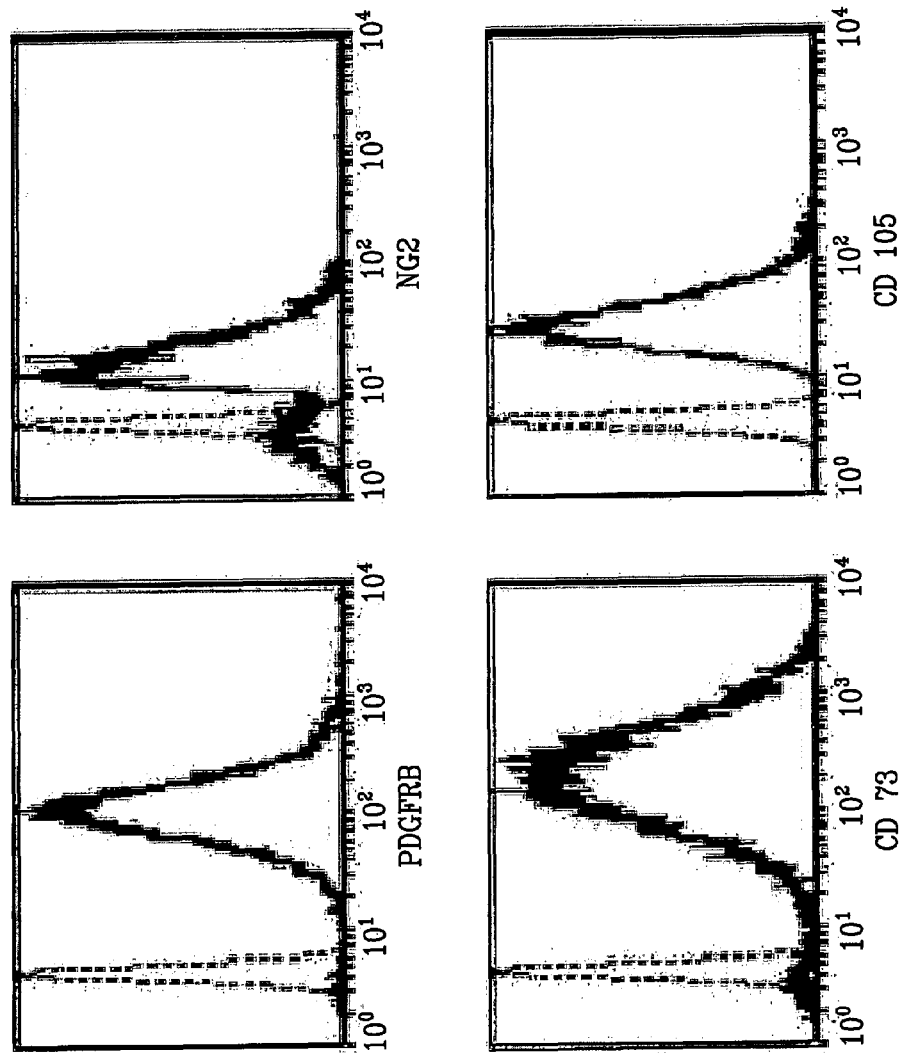
Figure 5C:
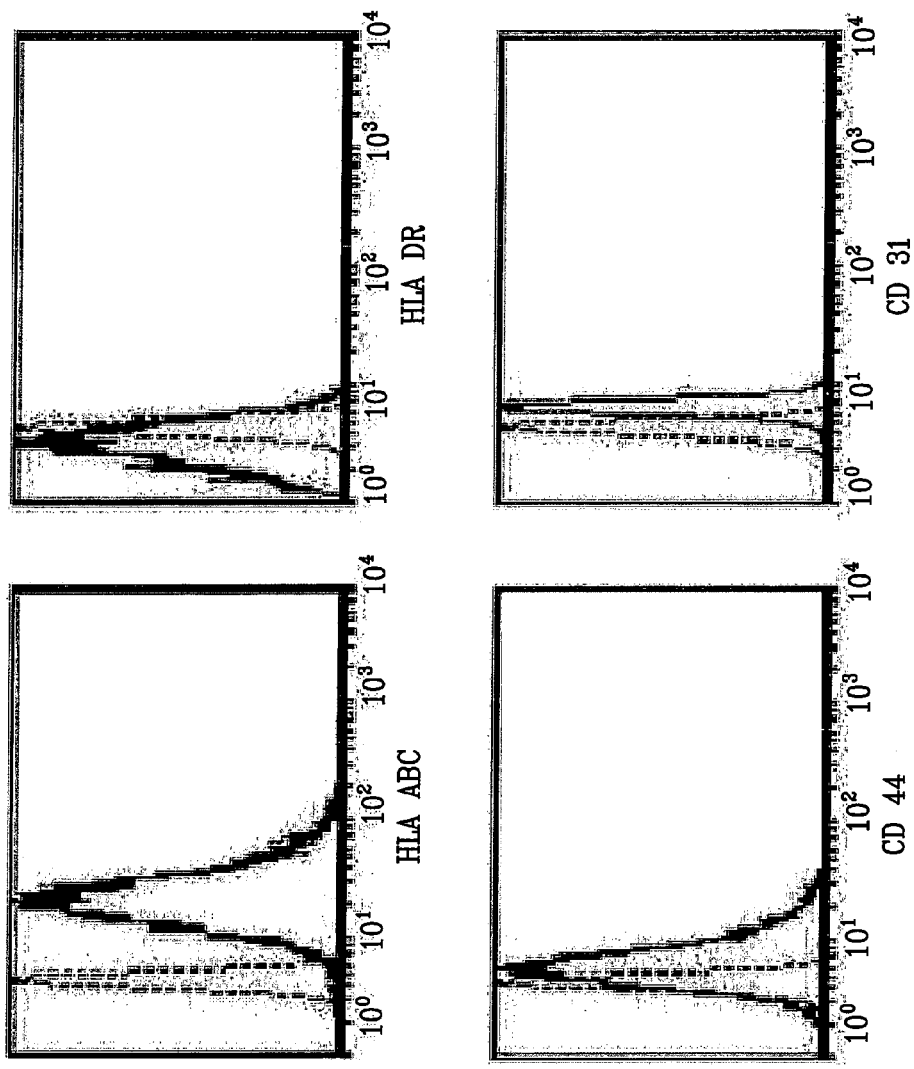
Figure 5D:
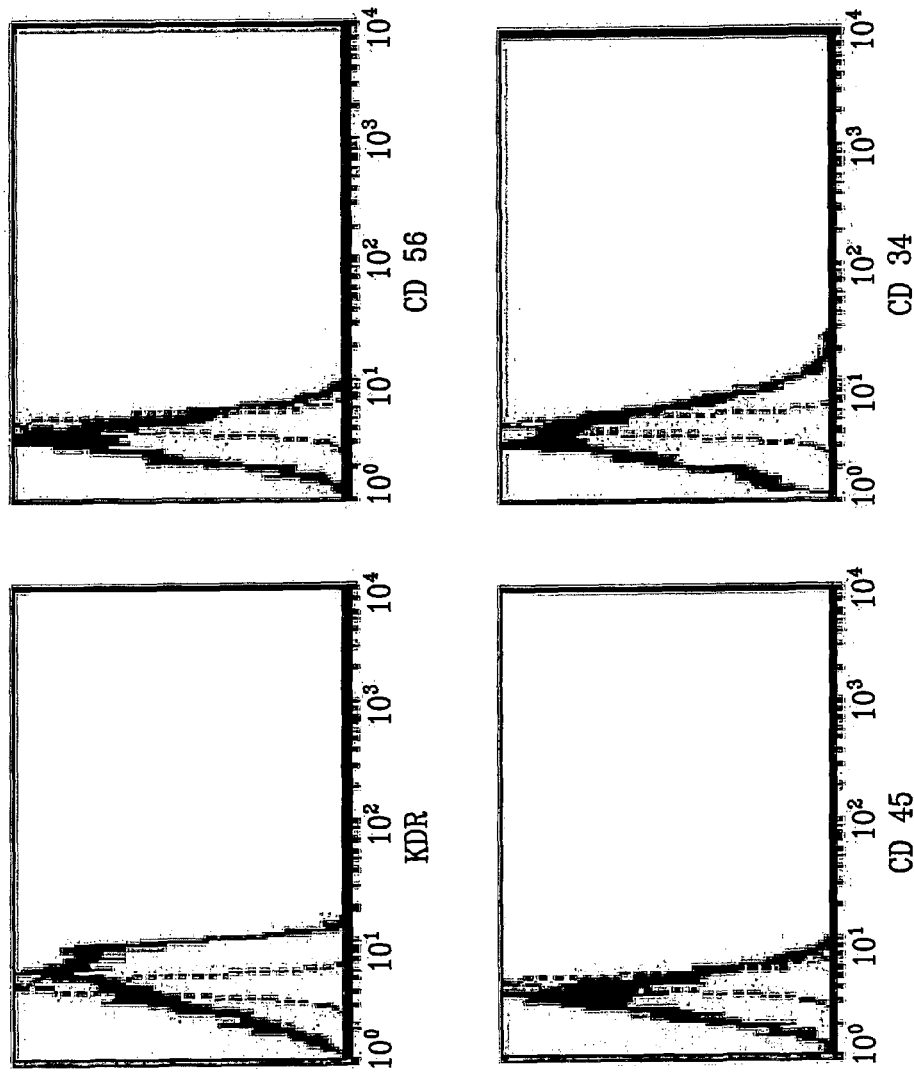

FIGS. 3A-B show the morphology of the mesenchymal stem cells isolated from the dental pulp of a fresh deciduous (non-exfoliated) tooth; in particular, FIG. 3A represents the mesenchymal stem cells at confluence; FIG. 3B represents a colony of mesenchymal stem cells defined as "round bottom";

FIGS. 3C-D show the morphology of the mesenchymal stem cells isolated from the dental pulp of a fresh deciduous (non-exfoliated), intact (non-pierced) tooth, thawed after cryopreservation in presence of DMSO (FIG. 3C) or without DMSO (FIG. 3D);

FIGS. 3E-F show the morphology of the mesenchymal stem cells isolated from the dental pulp of a decidous (non-exfoliated) tooth, thawed after piercing and cryopreservation according to the method of the present invention;

FIG. 4 shows the cumulative divisions of the population of mesenchymal stem cells isolated from the dental pulp of deciduous (non-exfoliated) teeth; MSC1 and MSC2: mesenchymal stem cells from pulp of fresh deciduous (non-exfoliated) tooth; MSC3: mesenchymal stem cells from deciduous (non-exfoliated), intact (non-pierced) tooth cryopreserved in presence of DMSO; MSC4: mesenchymal stem cells isolated from the pulp of deciduous (non-exfoliated), intact (non-pierced) tooth cryopreserved without DMSO; MSC5, MSC6 e MSC7: mesenchymal stem cells isolated from dental pulp of deciduous (non-exfoliated) tooth pierced and cryopreserved according to the method of the present invention; MSC8: mesenchymal stem cells isolated from dental pulp of fresh deciduous (non-exfoliated) tooth; said cells are subjected to a cryofreezing step in presence of DMSO and then to a thawing step.

FIGS. $5a$-$5b$-$5c$-$5d$ show the cytofluorimetric analysis of mesenchymal stem cells isolated from the dental pulp of deciduous (non-exfoliated) teeth.

Figure 1:
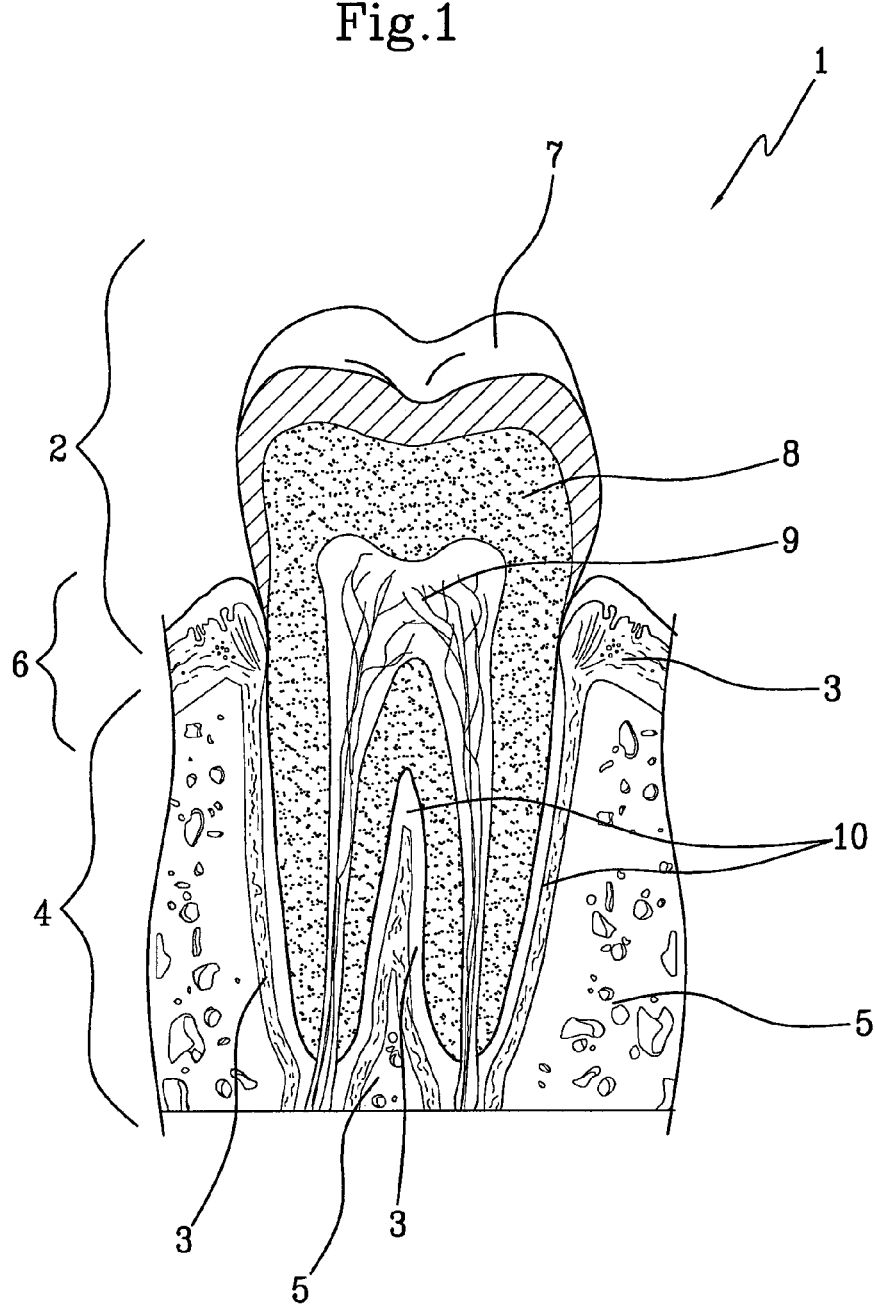
FIG. 1 shows the section of a molar tooth in its physiological seat.

In order to help understanding the present invention, FIG. 1 represents a section of a tooth, in particular of a molar tooth, located in its natural seat, the gingiva. Number 1 refers to a molar tooth as whole.

The tooth 1 comprises a crown 2 protruding from the gingiva 3, a root 4 anchored to the alveolar bone 5 and a neck 6 representing the transition area between the crown and the root.

The tooth is covered by a hard, mineralized layer of enamel 7, whose function is to protect the most delicate inner parts.

Below the enamel there is a hard layer of dentine 8, which makes up the greatest part of a tooth.

The innermost part of the tooth is made up of the dental pulp 9, which is highly sensitive to sudden temperature changes and consists of a highly vascularized, soft tissue.

In the mouth teeth are supported by the periodontium, made up of the gingiva surrounding the neck and covering the underlying bone, of a complex of fibers (defined as periodontal ligament; not shown in the figure) which can ensure a correct positioning of the tooth in the bone seat and, eventually, of the cementum 10 (coating the outside portion of the tooth root) and of the alveolar bone 5 (made up of the inner wall of the alveolus where the tooth is located).

Two series of teeth sprout in humans. The first series includes milk teeth, also known as temporary, reborner or, as used hereinafter in the present invention, deciduous teeth.

Deciduous teeth generally start erupting towards the sixth month and a two-year-old baby usually has 20 teeth.

The second series of teeth, or second teething or the equivalent term dentition, consists of permanent teeth.

The tooth germ from which permanent teeth develop lies inside the maxillary bones in a point corresponding to the deciduous teeth.

Around the sixth year of life of an individual, permanent teeth start developing and push away the teeth of the first series. This process can go on for six years (twenty years only for "wisdom teeth") and at the end of it an adult has thirty-two teeth. Mammals and humans have different types of teeth: incisors, canines, premolars and molars.

The present invention relates to a method for cryopreserving the pulp of a tooth, comprising the following steps:

(a) making at least one hole into said tooth so as to reach at least the dentine;

(b) put the tooth thus pierced in contact with a cryopreserving agent;

(c) adjusting the tooth in contact with the cryopreserving agent to a cryofreezing temperature.

The method is applied to a tooth isolated (ex vivo), extracted or removed from its natural seat.

The method according to the present invention can be applied to any tooth, preferably the tooth is a deciduous tooth, more preferably it is a deciduous, non-exfoliated tooth. In the framework of the present invention, non-exfoliated means a tooth removed or extracted from its natural seat before its physiological exchange. Moreover, the tooth advantageously used in the method according to the invention is a whole tooth including root/roots and crown.

The tooth can be a canine, an incisor or a molar, preferably a canine.

According to the present invention, the tooth can be isolated or removed or extracted from any individual. In particular, the method is applied to a tooth isolated or removed or extracted from an individual aged 6-20, preferably 5-14.

In a preferred embodiment of the invention, the tooth can belong to a healthy individual, without any systemic disease, or to an individual suffering from a systemic disease, preferably except for exanthematic diseases, or to an individual suffering from a genetic syndrome or disorder.

The method includes making at least one hole (or perforation) into a tooth, preferably with a laser. In a preferred embodiment, the number of holes can vary from 1 to 4 depending on the type of tooth. In particular, there can be 1 to 2 holes for a canine or an incisor, whereas 2 to 4 holes can be made onto a molar.

The hole is preferably a microhole (or microperforation); more preferably, it is a hole with a diameter of 0.001 to 0.5 mm, preferably 0.07 to 0.3 mm.

The hole (or perforation) is made so as to reach at least the dentine of said tooth.

In a preferred embodiment of the invention, the hole gets wholly through the enamel layer and partially through the dentine layer.

In another embodiment of the invention, the hole gets through the enamel and dentine layers and reaches the pulp layer without penetrating the pulp.

In another embodiment of the invention, the hole gets through the enamel and dentine layers and penetrates the pulp of a few microns, in particular the pulp is penetrated for a thickness of 3 to 30 microns, preferably 5 to 10 microns.

In both cases, the perforation does not get through the pulp but the enamel and dentine layers only.

It is advisable, when applying the method according to the invention, that the hole does not penetrate the pulp layer. However, in some cases, in particular when the method is applied using some types of laser (e.g. neodymium laser), it can be assumed that the pulp is penetrated for the thicknesses referred to above, without causing overheating and thus damages to the vitality of pulp cells.

In any case, both the condition in which the hole wholly gets through the dentine layer and the condition in which the hole only partially gets through the dentine enable the cryopreserving agent to access those tooth portions that are physiologically inaccessible. As a matter of fact, a tooth cannot as a rule be easily permeated by an agent (e.g. a cryopreserving agent according to the present invention) thanks to the hard enamel layer coating every tooth. This architecture makes the regions forming the tooth core (e.g. the pulp) hardly accessible and prevents an optimal cryopreservation of these regions.

Conversely, a tooth pierced according to the method of the present invention enables the cryopreserving agent to penetrate the tooth through the holes made and therefore makes it easier for the cryopreserving agent to permeate the tooth.

Figure 2B:
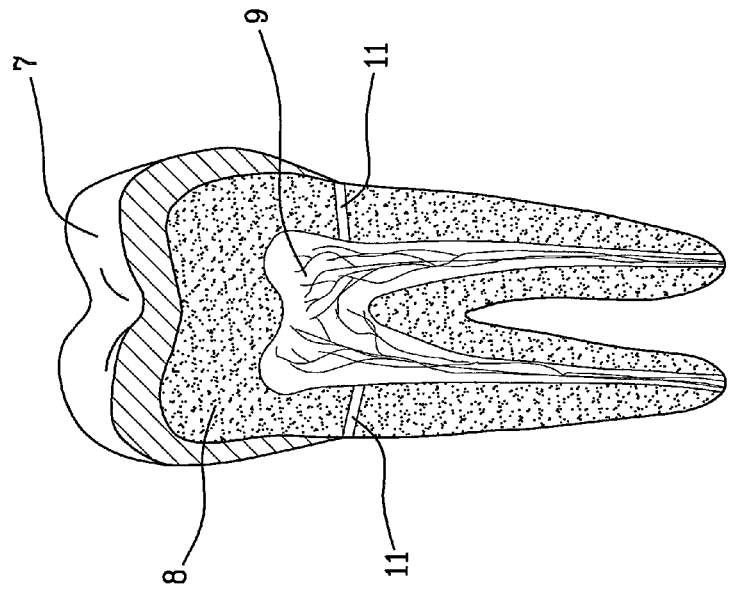
FIG. 2B represents a section of the tooth of FIG. 2A showing the path of the hole inside the tooth.
Figure 2A:
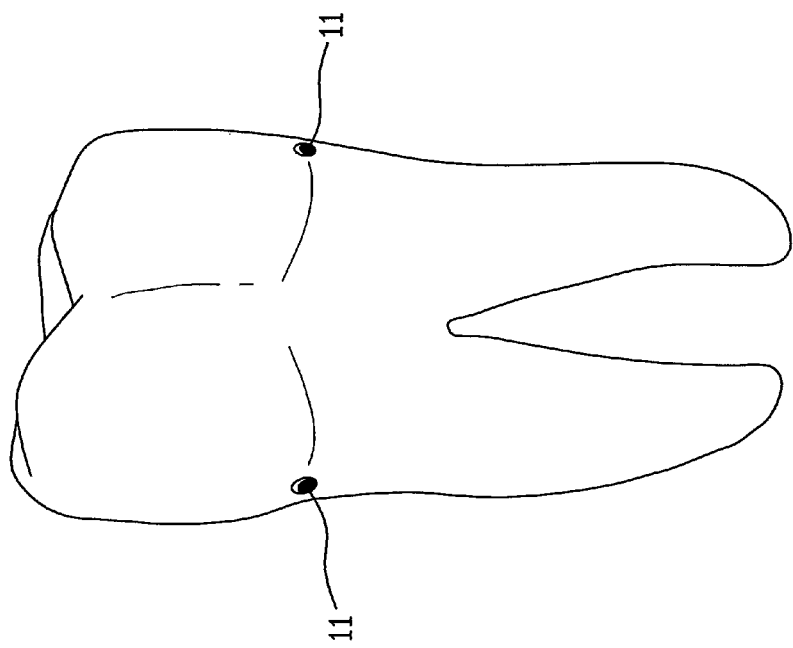
FIG. 2A shows a whole tooth extracted from the mouth and pierced with the method according to the present invention.

The perforation of the dental crown according to the invention is a non-through perforation, e.g. it does not get through the tooth from side to side (FIGS. 2A and 2B).

The hole is preferably made on the crown-root connection (neck).

In particular, FIG. 2A shows an embodiment of the invention relating to a molar tooth in which two holes 11 were made using the method according to the invention. The two holes are located on the tooth neck region.

FIG. 2B is a section of the molar tooth of FIG. 2A. In particular, the section shows a preferred path of the perforation, in which the hole wholly gets through the layers of enamel 7 and dentine 8 and reaches the pulp 9 without penetrating it.

The perforation of the tooth, according to the present invention, can be made straight after removing the tooth or at a later step.

In the latter case, the removed tooth will be preferably stored in a disinfecting, antibacterial and nutrient solution which enables to tooth to keep a good vitality until perforation.

Said nutrient solution can include a culture medium, e.g. RPMI, and/or fetal bovine serum and/or an antibiotic/antimycotic, e.g. a mixture of penicillin/streptomycin.

Preferably, the tooth extracted and immersed into the nutrient solution is stored in cold conditions, at a temperature of 0° C. to 10° C., preferably 2 to 6° C.

The perforation of the tooth is made with a laser having a suitable wavelength for piercing a hard tissue such as enamel and a hard and porous tissue such as dentine.

The laser advantageously used in the present invention has a wavelength of from 1064 to 10600 nm. Preferably, such laser has a fiber diameter of 200-700 μM; a pulse energy of 27-90 mJ; a power of 0.5-10 W; a frequency of 4-50 Hz. The laser can be used either in contact or not (preferably in contact), in continuous, pulsed or superpulsed mode.

The laser enables to eliminate first the substances that are most rich in water, allowing to remove in an extremely accurate and selective manner portions of dental enamel and dentin and to access root canals without running the risk of removing, tearing or overheating the pulp.

The main advantage of a laser having a wavelength of 1064 to 10600 nm lies precisely in the emitted wavelength, which represents the one required for working on dentine. Another advantage, beyond the reduction of the thermal increase on surrounding tissues, as already discussed above, is the possibility of limiting the range of action of laser light to very small areas; it is thus possible to work on the concerned area only without damaging surrounding dental tissues. Another advantage lies in that it does not produce vibrations and thus eliminates problems related to microfractures caused on dental tissues by the dynamic action of the drill. Beyond the photothermal action, the laser also performs a photomechanical action towards treated tissues. The operating mode makes the short pulse cause an energy peak in the application site, which unfolds as a pressure increase. This increase is followed by such a violent springback of the tissue as to result in the breaking of the connections and the detachment of tissue fragments. Thus, dental tissue removal is obtained as microexplosions; in other words, there is an explosion of tissue particles. Also in this case there is no thermal increase on the surrounding tissues.

The laser preferably used in the invention is therefore chosen among: neodymium, holmium, erbium, erbium-chromium and $CO_2$ lasers. Preferably, the laser used is selected between neodymium and erbium.

A neodymium laser (Nd:YAG) has as lasing medium an yttrium aluminum crystal (YAG) doped with neodymium atoms (Nd:$Y_3Al_5O_{12}$) and emits light with a wavelength of 1064 nm. This laser, when used according to the present invention, can pierce a tooth penetrating the pulp for a thickness of 5-10 µm.

A holmium laser (Ho:YAG) has as lasing medium an yttrium aluminum crystal (YAG) doped with holmium atoms (Ho:$Y_3Al_5O_{12}$) and emits light with a wavelength of 2100 nm.

An erbium laser (Er:YAG) is a solid-state laser, whose lasing medium is an synthetic garnet, yttrium and aluminum crystal doped with erbium atoms, and emits light with a wavelength of 2940 nm.

An erbium-chromium laser (YSGG) has as lasing medium an yttrium, scandium and gallium crystal doped with erbium and chromium atoms, and emits light with a wavelength of 2780 nm.

A $CO_2$ laser has a solid-state lasing medium, with a wavelength of 9600 to 10600 nm.

The tooth is pierced with a laser preferably keeping the tooth in a suitable position so as to be pierced with dental pliers.

After perforation, the pierced tooth is contacted with a cryopreserving agent, preferably by immersion in said cryopreserving agent.

The pierced tooth is preferably contacted with the cryopreserving agent for a time of 5 minutes to 1 hour, preferably 10-30 minutes.

The pierced tooth is preferably contacted with or immersed in the cryopreserving agent at a temperature of 0-10° C., more preferably 2-6° C.

The purpose of the last two steps is to enable to cryopreserving agent to wholly permeate the tooth through the holes made therein.

Although DMSO; glycerol and triol are the preferred cryopreserving agents, in particular DMSO, one or more of the following cryopreserving agents can be used to the same purpose: sucrose, trialose, lactose, ethylene or propylene glycol, dextran, hydroxyethyl starch, polyvinylpyrrolidone, formamide, 1,2-propanediol, ethanol, methanol or polyethylene.

The tooth pierced and contacted with the cryopreserving fluid is then subjected to cryofreezing.

Cryofreezing occurs at a temperature of −15° C. to −196° C., preferably −50 to −90° C.

In a preferred embodiment, cryofreezing is executed with a programmed temperature drop until reaching the required temperature at which the sample will be stored for the desired time (i.e. until an individual needs to recover stem cells for therapeutic uses). By way of example, the temperature can be lowered of 1-5 degrees a minute.

Cryopreservation can be executed straight after piercing the tooth or at a later step. In the latter case, the pierced tooth can be stored in a suitable container in cold conditions, preferably at a temperature of 2 to 10° C. The preservation step can last for a maximum time of 48-72 hours.

In another aspect, the invention relates to a cryopreserved isolated tooth, in particular with the method according to the present invention, characterized by at least one hole made, preferably with a laser, so as to reach at least the dentine. Said hole is preferably made on the crown-root connection (neck).

Said tooth is cryopreserved in contact with a cryopreserving agent, preferably DMSO.

Said tooth is used, after thawing and breaking, to isolate cells of the dental pulp, in particular stem cells, preferably mesenchymal stem cells.

In another aspect, the invention relates to an (isolated) cell population that can be obtained from the cryopreserved dental pulp according to the method of the present invention.

Said cell population comprises isolated stem cells, preferably isolated mesenchymal stem cells (MSCs) deriving from the dental pulp.

In particular, in order to obtain said cell population, the cryopreserved tooth according to the present invention can be thawed. Preferably, tooth thawing can be executed at a temperature of 30-45° C.

In this step it is preferred to dilute or remove the cryopreserving agent in the thawed sample, e.g. by means of at least a step of contacting with a washing solution. The washing solution can be e.g. PBS.

Then the thawed tooth can be broken or crushed or ground, e.g. with a mechanical device, preferably by means of a press or a nutcracker.

In the tooth breaking step it preferred to lever with the mechanical device used on the tooth perforation point or points. Being weaker in these points, the tooth will give up more easily to the breaking action.

Once the tooth is crushed, the pulp is extracted, preferably using sterile pliers and working in general sterile conditions.

The dental pulp thus extracted is then subjected to dissociation using any technique known in the field.

For instance, dissociation can be mechanical or dissociation or digestion can be enzymatic.

Examples of enzymes that can be used for dissociation are chosen among: trypsin, collagenase, hyaluronidase or cellulase mixtures.

Dissociation can be executed at a temperature varying from 32 to 40° C.

The duration of the dissociation step can vary from 30 minutes to 2 hours. Dissociation ends when the dental pulp sample is fully separated into its cell components.

The dental pulp sample can be subjected to a washing step. The washing step can be executed with one or more agents selected from the group comprising: PBS, HBSS, with and without calcium and magnesium, added (or not) with glycine, alanine, glucose, insulin, EDTA or EGTA or albumin or dextran or a culture medium, e.g. RPMI.

The cells of the dental pulp thus recovered, i.e. stem cells, in particular mesenchymal stem cells, are subjected to a step of amplification in culture, using any technique known in the field.

For instance, the culture can include a step of cell seeding on a suitable support (e.g. plastic plates or flasks), in a suitable culture medium.

The density with which the cells of the dental pulp can be seeded is of 1000-1000000 cells/$cm^2$, preferably 5000-7000 cells/$cm^2$.

The culture medium is selected among: alpha MEM glutamax, MEM, DMEM, alpha MEM, RPMI, Iscove's and F1.

The medium can be added with various nutrients such as supplements, e.g. Fetal Bovine Serum, non-essential amino acids, L-glutamine, growth factors chosen in the group comprising EGF, FGF, VEGF and HGF, or a platelet gel.

The medium can also contain antibiotics and/or antimycotics, e.g. gentamicin, penicillin and streptomycin.

For instance, the culture medium can include alpha MEM glutamax, preferably enriched with fetal bovine serum and/or penicillin/streptomycin.

Cell culture can be executed under controlled temperature, humidity and/or $CO_2$ pressure conditions.

In particular, temperature can oscillate from 25 to 37° C.; relative humidity varies from 80 to 98%, pressure is preferably atmospheric pressure; $CO_2$ pressure can vary from 3 to 10%.

Cells growing in adhesion are dissociated from the cells thus cultivated.

Dissociation can occur as described above; preferably, cell dissociation can be executed enzymatically, more preferably with the enzyme collagenase A.

The cell population obtained after in-vitro cultivation comprises cells of the dental pulp, in particular stem cells, preferably mesenchymal stem cells.

A further object of the present invention is an isolated population of mesenchymal stem cells deriving from dental pulp of a cryopreserved tooth after laser perforation according to the present invention, with a proliferation rate of 4 to 4.5, said proliferation rate being calculated as cumulative doublings of the population (CDP) over a time of ten days.

In another embodiment, said mesenchymal stem cells express the following marker panel CD90, CD73, CD105, CD44 and HLA-ABC, CD146, NG2, PDGF-Rbeta, alpha-SMA and, preferably, do not express the following marker panel CD34, CD45, CD56, CD31, CD144, KDR and HLA-DR.

In a preferred embodiment, said mesenchymal stem cells can be obtained from the cryopreserved dental pulp according to the method of the present invention.

Said mesenchymal stem cells can be differentiated into cells of mesodermal origin, in particular they can generate adipose, cartilage or bone cells.

A further object of the invention includes: a population of cells differentiated from said mesenchymal stem cells; a population comprising mesenchymal stem cells deriving from dental pulp (preferably cryopreserved pulp according to the method of the invention) and differentiated mesenchymal stem cells.

Another aspect of the invention relates to the use of the mesenchymal stem cells of the invention for generating in situ or ex situ differentiated cells, preferably of osteogenic or chondrogenic or adipogenic type.

These mesenchymal stem cells and/or the differentiated mesenchymal stem cells are used as a medicament, preferably for autologous or allogenic transplantation.

As an alternative, these mesenchymal stem cells and/or the differentiated mesenchymal stem cells are used for treating degenerative diseases of bone or cartilage tissue, or in tissue engineering of bones, cartilage, intervertebral discs, muscle, marrow stroma, sinews, fat tissue, tooth-associated tissues and other connective tissues.

Said tooth-associated tissues are preferably of ectodermal origin, more preferably they include enamel, cementum (a tissue strongly resembling bone tissue), dentine and pulp.

Said mesenchymal stem cells and/or the differentiated mesenchymal stem cells, according to the present invention, can be used in cell therapy for dental applications such as e.g. bone regeneration, which can be performed also by autologous transplantation on maxillo-facial areas, e.g. on mandible and jaw bones.

The mesenchymal stem cells and/or the differentiated mesenchymal stem cells according to the present invention can be further used in regenerative or replacement medicine after a trauma, a disease or aging.

EXAMPLE

Selection of "Donor" Patients
Inclusion Criteria
Children ages 7 to 11 years;
Deciduous teeth;
Intact radicular processes;
Supplemental dental elements
Exclusion Criteria
Carious processes
Dental crown previously treated with amalgam and composites
Previous pulpotomies and pulpectomies
Radicular or apical resorption
Periapical injuries
"Non-vital", devitalized dental elements
Severe bruxism
Systemic diseases
Teeth Selection
Teeth used are canines and incisors.
Extraction of Deciduous Teeth.

The deciduous teeth, not exfoliated yet, are removed from the oral cavity after local anesthesia (anesthesia type and anesthetic are decided based on the age and health of the subject).

Once the dental elements are extracted, residues of gingiva or periodontal ligament, if any, are removed with a sterile gauzed imbibed with physiological solution. After carefully decontaminating the outer surface, the tooth is immersed in a 5 ml polypropylene vial containing the suitable culture medium (RPMI-20%-FBS-1%-penicillin/streptomycin) and is stored in a refrigerator at 4° C. in vertical position.

Preparation of the Isolated Dental Element.

The tooth is:
taken from the vial with dental pliers;
kept at the same height as the crown edges using the pliers tips;
with a Nd:YAG laser two non-through holes are made on the radicular canal under the root-crown connection.

For canines and incisors it was decided to make two hole only so as to prevent the tooth from overheating, though removing at the same time part of the enamel and the dentine in order to help penetration of the cryopreserving agent into the dental pulp and subsequent tooth opening.

The laser used has the following parameters:
wavelength=1064 nm,
fiber diameter=320 μm,
pulse energy=40 mJ,
power=0.7/1.7 W,
frequency=10 Hz,
it is not focused but diverges of 20°, therefore the point with the highest concentration is on the surface and must thus be used in contact.

Tooth Transport.

After piercing, the tooth is introduced into a sterile, non-cytotoxic, apyrogenic 2 ml cryogenic vial (cryovial) made of polypropylene, with screwed plug with outer threading made of high density polyethylene. The vial contains inside the culture medium as described above. The vial is fitted into a vial-holding box made of polystyrene so as to keep the tooth in vertical position.

From piercing to transport, the tooth is stored in a refrigerator at 4° C.

Banking of the Isolated Deciduous Tooth.

Within 48-72 from the removal, the tooth is transferred with disposable pliers into a 2 ml cryovial containing a cryopreserving solution (10% DMSO-90% dextran).

The vial is stored for 20 minutes at 4° C. so as to allow the cryopreserving agent to penetrate the tooth. The cryovial is then introduced into a device containing propyl alcohol, which enables a controlled temperature fall. Then the vial containing the tooth is put into a mechanical freezer at −80° C. for at least 12 hours.

The device containing isopropyl alcohol enables a controlled temperature fall at a cooling rate of −1° C./min. This cooling rate defines the ideal kinetics for a good cryopreservation and a good cell recovery.

Thawing and Breaking of the Isolated Deciduous Tooth.

The tooth is thawed and the dental pulp is extracted with the following steps:
- introduction of the tooth into a sterile bag;
- introduction of the bag containing the tooth into a bath with continuous stirring at 37° C. for 3 minutes;
- introduction of the tooth into a vial containing 10 ml PBS so as to enable DMSO dilution;
- mechanical breaking of the tooth;
- pulp extraction with disposable sterile pliers and introduction into a container tube.

Morphology of Mesenchymal Stem Cells Isolated from the Dental Pulp of: a Fresh (Non-Cryopreserved) Deciduous (Non-Exfoliated) Tooth; an Intact (without Holes) Cryopreserved Deciduous (Non-Exfoliated) Tooth; a Cryopreserved Deciduous (Non-Exfoliated) Tooth after Laser Piercing According to the Method Described Above.

A sample of dental pulp obtained after crushing of: a fresh deciduous tooth (not subjected to cryopreservation); an intact deciduous tooth cryopreserved with or without DMSO; a deciduous tooth cryopreserved after laser piercing according to the method described above, was digested with collagenase A 1 mg/ml (Roche Diagnostics GmbH; Mannheim, Germany) at a temperature of 37° C. for 1 hour until complete sample dissociation.

After sample digestion the suspension of dental pulp cells was gathered and diluted in a phosphate buffered saline (PBS; Gibco, Grand Island, N.Y., USA); then the diluted cell suspension was centrifuged at 1400 rpm for 10 minutes. The cell pellet was resuspended and the obtained cells were sown in a culture medium comprising: Alpha-MEM glutamax 1% (Introvigen, Carlsdad, Calif., USA), 20% Fetal Bovine Serum (FBS; Biochrom AG, Berlin, Germany), 1% penicillin/streptomycin (P/S, Sigma-Aldrich; St. Louis, Mo., USA).

The culture medium was replaced with fresh medium every 3 days and the mesenchymal stem cells deriving from the dental pulp were grown under long-term conditions at 37° C. in humidified atmosphere containing 5% $CO_2$.

The mesenchymal stem cells isolated from the dental pulp of samples of fresh deciduous tooth can be kept in culture in long-term conditions, showing a spindle-like shape (FIG. 3A) and forming colonies defined as "round bottom" (FIG. 3B). The mesenchymal stem cells isolated from the dental pulp of samples of intact deciduous tooth cryopreserved with DMSO (FIG. 3C) or without DMSO (FIG. 3D) can be kept in culture but the cells are obviously apoptotic and suffering.

The mesenchymal stem cells isolated from the dental pulp of samples of deciduous tooth cryopreserved following laser piercing according to the method described above (FIGS. 4E-F), can proliferate and show the typical spindle-like shape of mesenchymal stem cells isolated from fresh tooth.

Proliferation and Expansion of Mesenchymal Stem Cells Isolated from the Dental Pulp of a Fresh or Cryopreserved Deciduous (Intact and Pierced) Tooth.

When the cells deriving from the dental pulp of a tooth, which grow adhering to the surface onto which they are plated (generally a variously sized plate or flask), reach a confluence of 80%, they are removed from the adhesion surface by a treatment with trypsin-EDTA (Gibco), counted and seeded again into a 75 $cm^2$ flask at a concentration of 5000-7000 cells/$cm^2$ under the culture conditions described above. At each step of the cell culture, every cell count and dilution was recorded and used to calculate the potential expansion in terms of number of cumulative doublings of cell population (CPD).

The number of cell doublings (PD) was calculated by solving the following equation:

$$PD = \log(N)/\log 2$$

wherein N represents the difference between the number of cells gathered after the treatment with trypsin (Ni) and the number of seeded cells (NO). The CPD was calculated as the sum of the PDs that occurred during the 70 days of long-term culture.

The growth of the mesenchymal stem cells deriving from the samples of fresh deciduous tooth is always very high during the whole culturing phase (see FIG. 4, MSCs1 and MSCs2), even after the isolated cells were subjected to a cryofreezing step (MSCs8). The proliferation rate of the mesenchymal stem cells deriving from the samples of intact deciduous tooth cryopreserved with or without DMSO, though without being subjected to the piercing treatment described above, has proven to be always very low (see FIG. 4, MSCs3 and MSCs4).

The proliferation rate of the mesenchymal stem cells deriving from the samples of deciduous tooth cryopreserved after laser piercing according to the method described above, is similar to the one of cells extracted from the fresh tooth (see FIG. 4, MSCs5, MSCs6 and MSCs7).

In particular, the cell population of mesenchymal stem cells deriving from the dental pulp is characterized by a high proliferation rate as determined by calculating the cumulative population doublings (CPD), which for a culture time of ten days is very high in the case of mesenchymal stem cells isolated from fresh non-cryopreserved teeth (mean value 5.3), of mesenchymal stem cells isolated from teeth cryopreserved after laser piercing according to the invention (mean value 4.1), and of mesenchymal stem cells isolated from fresh teeth and subjected to cryopreservation (mean value 5.1).

In the case of mesenchymal stem cells isolated from teeth cryopreserved without laser piercing, characterized by a low proliferation rate, it was possible to calculate CPD after 40 days of culture (mean value 2.5).

Cytofluorimetric Analysis of Mesenchymal Stem Cells Isolated from the Dental Pulp of a Fresh Deciduous Tooth and of a Cryopreserved Deciduous Tooth Subjected to Piercing According to the Present Invention.

The mesenchymal stem cells isolated from samples of fresh deciduous tooth or of cryopreserved deciduous tooth subjected to piercing according to the invention, were characterized by means of cytofluorimetric analysis during the various culture steps (FIGS. 5a-5b-5c-5d).

The cells were washed with PBS for 20 minutes at room temperature (RT) and then incubated under dark conditions with the following conjugated mouse anti-human antibodies: CD31-PE (Becton Dickinson, BD, San Jose, Calif., USA), CD34-PE (BD), CD44-FITC (BD), CD45-PC7 (Beckman Coulter, Fullerton, Calif., USA), CD73-PE (BD), CD90-PE (Chemicon, Temecula, Calif., USA), CD105-PE (Immuno-Tools, Friesoythe, Germany), CD146-PE/FITC (BioCytex, Marseille, France), alpha-SMA FITC (Sigma-Aldrich), NG2-PE (Beckman Coulter), PDGF-Rbeta PE (BD), HLA- ABC-FITC (BD), HLA-DR-PE (BD), CD144-FITC (VE-cadherin; Bender MedSystem, Burlingame, Calif., USA), KDR-PE (BD).

The various isotypes of conjugated immunoglobulins were used as negative control: IgG1 PE-FITC (Chemicon), IgG1-PC7 (Beckman Coulter) and IgG1-APC (BD). After incubation with the antibodies, the cells were washed with PBS containing Bovine Serum Albumin (BSA) 0.1%.

Using a cytofluorimeter Cytomics FC500 (Beckman Coulter) at least 50,000 events were acquired and the graphs of FIGS. 5a-5b-5c-5d were generated by analysis with CXP software.

The mesenchymal stem cells isolated from samples of fresh deciduous tooth or of cryopreserved deciduous tooth pierced according to the invention, cultivated in step 3, were removed from the flasks using trypsin and characterized by cytofluorimetry. The mesenchymal stem cells isolated both from samples of fresh deciduous tooth and from samples of cryopreserved deciduous tooth pierced according to the present invention, have shown the typical immunophenotype of mesenchymal stem cells, namely: $CD90^+$, $CD73^+$, $CD105^+$, $CD44^+$ and $HLA\text{-}ABC^+$.

These cells also express CD146, NG2, PDGF-Rbeta, alpha-SMA, but not CD34, CD45 and CD56.

Moreover, these cells are negative for the expression of CD31, CD144, KDR and HLA-DR, thus confirming their typical profile of mesenchymal stem cells (FIGS. 5a-5b-5c-5d). Therefore, the mesenchymal stem cells isolated from deciduous tooth pierced and cryopreserved according to the present invention, are characterized by the following immunophenotype: $CD90^+$, $CD73^+$, $CD105^+$, $CD44^+$, $HLA\text{-}ABC^+$ $CD146^+$, $NG2^+$, $PDGF\text{-}Rbeta^+$ and $alpha\text{-}SMA^+$. Moreover, they are $CD34^-$, $CD45^-$, $CD56^-$, $CD31^-$, $CD144^-$, $KDR^-$ and $HLA\text{-}DR^-$.

The same percentages of the markers listed above were found also in the cells at the sixth culture step.

In particular, the analyzed markers are: CD146, alpha-SMA (SMA), PDGFRbeta (PDGFRB), CD90, CD44, CD73, HLA-ABC, HLA-DR, CD105, KDR, CD144, CD31, CD45 and CD34. The cells are positive for: CD90, CD73, CD105, CD44, HLA-ABC, CD146, NG2, PDGFRB, SMA.

The cells are negative for: CD34, CD45, CD56, CD31, CD144, KDR and HLA-DR.

Differentiation of Mesenchymal Stem Cells Isolated from the Dental Pulp of a Fresh Deciduous (Non-Exfoliated) Tooth.

The mesenchymal stem cells isolated from the dental pulp of a fresh deciduous tooth were differentiated adipogenically and osteogenically using suitable culture media.

In order to induce adipogenic differentiation, the mesenchymal stem cells were plated at a cell density of $2.1 \times 10^4$ cells/cm$^2$ in a medium known as human MSC Adipogenic Induction and Maintenance (art. no. PT-3102B/PT-4135 and PT-3102A/PT-4122-Lonza).

When the cells reached confluence, 3 induction/maintenance cycles were executed, then the mesenchymal stem cells were cultured for 7 days more in the added medium known as Adipogenic Differentiation Maintenance Medium (Lonza), replacing the culture medium every 2-3 days.

The cells were stained with Oil Red O solution (Sigma-Aldrich) so as to show lipidic vacuoles.

In order to differentiate osteogenically the mesenchymal stem cells isolated from the dental pulp of a fresh deciduous tooth, $3.1 \times 10^3$ cells/cm$^2$ were grown for 3 weeks in a medium known as human MSC Osteogenic Medium (art. no. PT-3924/PT4120 Lonza).

The cells induced to osteogenic differentiation were first fixed with 70% ethyl alcohol for 1 hour and then stained for 10 minutes with Alizarin Red S 40 mM (Sigma-Aldrich) in order to show calcium deposits.

The images of the colorimetric assays were acquired with Nikon Eclipse TS 100 microscope equipped with lenses 40×/0.55 Ph1 ADL and 20×/0.40 Ph1 ADL, and the photographs were acquired with Nikon Digital Slide DS-L1 camera.

The mesenchymal stem cells isolated from the dental pulp of a fresh deciduous tooth can differentiate, under a suitable differentiative stimulus, into cells of the osteogenic and adipogenic lineage.

Under osteogenic differentiation conditions, the mesenchymal stem cells isolated from the dental pulp of a fresh deciduous tooth mineralize with Alizarin red staining specific for calcium deposit. Under adipogenic differentiation conditions, the mesenchymal stem cells isolated from the dental pulp of a fresh deciduous tooth generate lipidic vacuoles after 2 weeks.

The invention claimed is:

1. A method for cryopreserving a pierced tooth comprising an intact whole tooth containing dental pulp below a tooth crown and dentine, comprising the following steps:
    a) making at least one non-through hole with a laser having a wavelength from 1064 nm to 10600 nm into said tooth so as to reach at least the dentine, but not the pulp;
    b) placing the pierced tooth thus pierced in contact with a cryopreserving agent;
    c) adjusting the pierced tooth in contact with the cryopreserving agent to a cryofreezing temperature of −15° C. to −196° C.

2. The method according to claim 1, wherein said tooth is a deciduous tooth.

3. The method according to claim 2, wherein said tooth is a non-exfoliated deciduous tooth.

4. The method according to claim 1, wherein said tooth is an isolated tooth of a person aged 6-20 years.

5. The method according to claim 1, wherein said at least one hole is made in the area of the collar of said tooth.

6. The method according to claim 1, wherein said at least one hole is 1 to 4 holes.

7. The method according to claim 1, wherein said at least one hole has a diameter of 0.001 to 0.5 millimeters.

8. The method according to claim 7, wherein said diameter is 0.07 to 0.3 mm.

9. The method according to claim 1, wherein said cryopreserving agent is selected from the group consisting of DMSO, glycerol, triol, sucrose, trialose, lactose, ethylene glycol, propylene glycol, dextrane, hydroxyethyl starch, polyvinylpyrrolidone, formamide, 1,2-propanediol, ethanol, methanol and polyethylene.

10. The method according to claim 1, further comprising a step of thawing the tooth and/or of breaking the tooth and/or of isolating stem cells from tooth pulp.

11. The method according to claim 1, wherein said tooth is an isolated tooth of a person aged 5-14 years.

12. The method according to claim 1, wherein said at least one hole into said tooth is 1 to 2 holes in a canine or incisor tooth.

13. The method according to claim 1, wherein said at least one hole into said tooth is 2 to 4 holes in a molar tooth.

14. The method according to claim 1, wherein the laser is selected from the group consisting of neodymium, holmium, erbium, erbium/chrome and $CO_2$ lasers.

15. The method according to claim 1, wherein the laser is selected from the group consisting of erbium and neodymium lasers.

16. The method according to claim 9, wherein said cryopreserving agent is DMSO.

17. The method according to claim 1, wherein said temperature is −50° C. to −90° C.

* * * * *